United States Patent [19]
Heinonen et al.

[11] Patent Number: 5,840,020
[45] Date of Patent: Nov. 24, 1998

[54] MONITORING METHOD AND A MONITORING EQUIPMENT

[75] Inventors: Pekka Heinonen; Harri Okkonen, both of Espoo, Finland

[73] Assignee: Nokia Mobile Phones, Ltd., Finland

[21] Appl. No.: 795,206

[22] Filed: Feb. 5, 1997

[30]  Foreign Application Priority Data

Feb. 12, 1996 [FI] Finland .................................... 960637

[51] Int. Cl.⁶ ........................................................ A61B 5/00
[52] U.S. Cl. .......................... 600/309; 600/365; 128/904; 128/920
[58] Field of Search ..................................... 128/903, 904, 128/920, 923; 600/300, 309, 365, 368

[56]  References Cited

U.S. PATENT DOCUMENTS

| | | |
|---|---|---|
| 4,731,726 | 3/1988 | Allen, III . |
| 4,871,351 | 10/1989 | Feingold . |
| 5,216,597 | 6/1993 | Beckers . |
| 5,251,126 | 10/1993 | Kahn et al. . |
| 5,462,051 | 10/1995 | Oka et al. . |
| 5,544,661 | 8/1996 | Davis et al. ............................ 128/904 |

FOREIGN PATENT DOCUMENTS

| | | |
|---|---|---|
| 0 199 484 A3 | 10/1986 | European Pat. Off. . |
| 0 483 595 A3 | 5/1992 | European Pat. Off. . |
| 42 21 848 | 1/1994 | Germany . |
| 44 15 896 A1 | 11/1995 | Germany . |
| WO 90/08361 | 7/1990 | WIPO . |

OTHER PUBLICATIONS

"A Telemedicine Distributed Decision–Support System for Diabetes Management", Proceedings of the Annual International Conference of the IEEE Engineering in Medicine and Biology Society, vol. 14, Nov. 1992, (Paris, France), pp. 1238–1239, E.J. Goméz et al.

*Primary Examiner*—Max Hindenburg
*Assistant Examiner*—Eric F. Winakur
*Attorney, Agent, or Firm*—Finnegan, Henderson, Farabow, Garrett, & Dunner, L.L.P.

[57]  ABSTRACT

Monitoring equipment including means for receiving a measurement result indicating the patient's blood glucose level, and for staring it in a first memory means. In order to improve and facilitate the treatment of the patient, the monitoring equipment further includes means for receiving data concerning the patient's diet, medication and physical strain, and for storing it in the first memory means, data processing means for calculating a predictive value on the basis of the data stored in the first memory means, and corrector means for calculating the difference between the calculated predictive value and the patient's actual blood glucose level, and for correcting the mathematical model utilized to calculate the predictive value in order to take into account the aforementioned difference in subsequent calculations of predictive values.

7 Claims, 1 Drawing Sheet

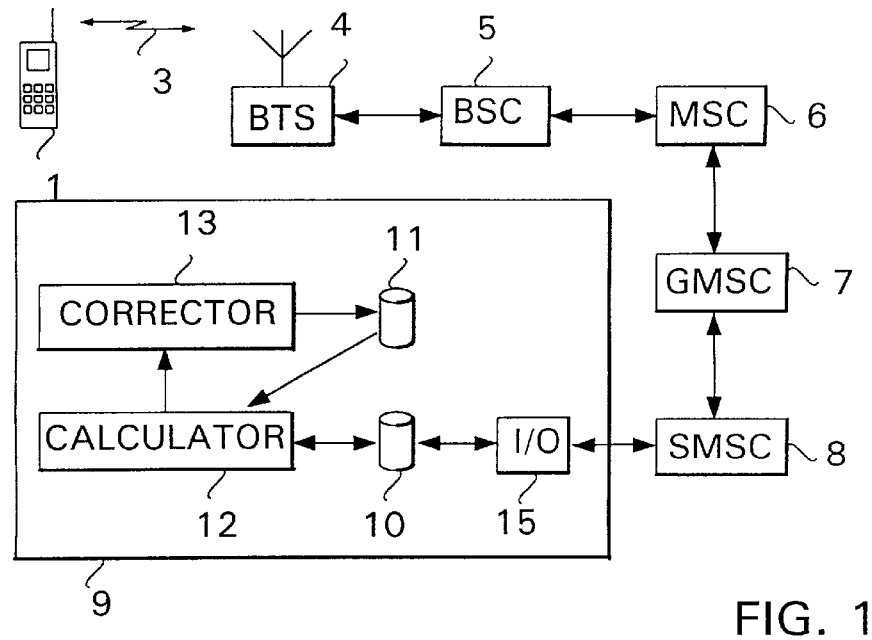
FIG. 1
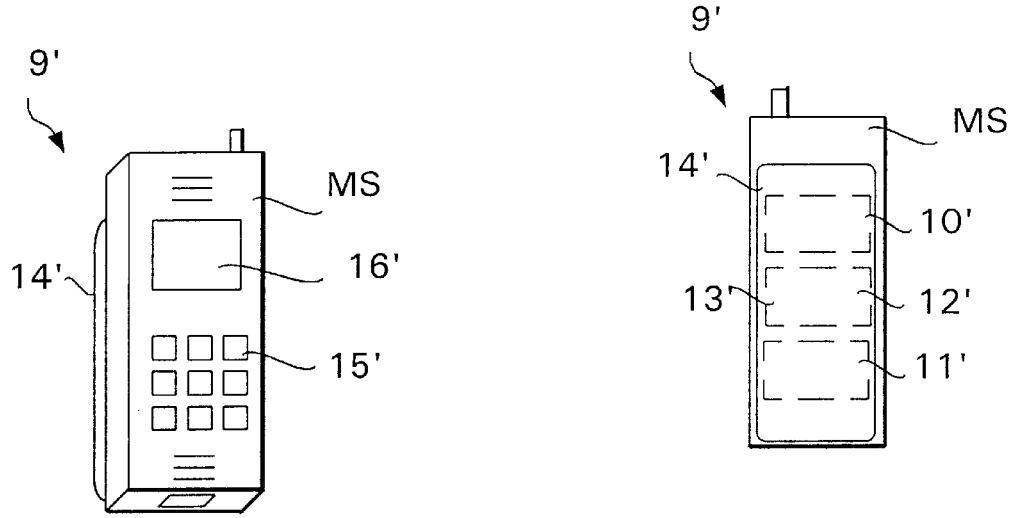
FIG. 2
FIG. 3
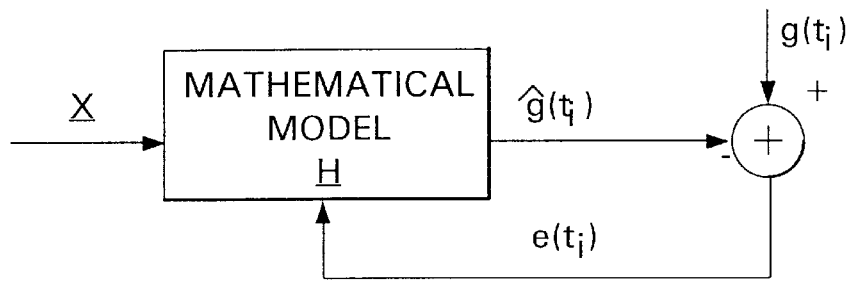
FIG. 4

MONITORING METHOD AND A MONITORING EQUIPMENT

FIELD OF THE INVENTION

The present invention relates to a method for monitoring the health of a patient, wherein the glucose level of the patient's blood sample is measured. The invention also relates to a monitoring equipment for monitoring the health of a patient, the equipment comprising means for receiving a measurement result indicating the glucose level in the patient's blood sample and for storing it in a first memory means together with data indicating the moment of the measurement.

DESCRIPTION OF THE PRIOR ART

As is well known, monitoring the health of a patient with diabetes is primarily based on the measurement of the patient's blood glucose level at regular intervals. Treating diabetes requires regular measurements and regular monitoring of the measurement results in order to ensure that the patient's blood glucose level definitely remains within the allowable area and that the patient's medication is optimal.

In the present health care system it is not possible for financial and practical reasons for a person specialized in treating diabetes to personally monitor continuously the health of a patient, but the monitoring of the patient's health is largely dependent on the patient himself. Therefore the patient himself must perform measurements at regular intervals, even as often as 6 to 8 times a day. In order that the doctor treating the patient could obtain data about the development of the patient's health over a longer period, the patient must also keep a record of the measurement results, which the doctor can examine afterwards.

The fact that a relatively large number of patients with diabetes also contract a secondary disease (e.g. cardiovascular diseases, neuropathy or blindness), which in turn causes considerable costs for the society, clearly indicates that at the moment doctors cannot treat patients with diabetes sufficiently effectively or cannot help the patients to care for themselves. One reason for this is that each doctor often treats a high number of patients, whereupon the contact between each individual patient and the doctor is insufficient and the doctor cannot therefore monitor the development of the health of individual patients sufficiently effectively.

SUMMARY OF THE INVENTION

The purpose of the present invention is to facilitate and improve the treatment of a patient with diabetes and to provide a method by means of which the patient is able to care for himself more effectively than previously. This object is achieved with a method according to the invention, characterized by formulating an adaptive mathematical model about the behaviour of the patient's blood glucose level, the model taking into account at least the patient's diet, medication and physical strain and comprising comparing the predictive values provided by the model to the measured glucose levels and correcting the mathematical model on the basis of the result of said comparison, and providing the patient with means for utilizing said mathematical model, so that the patient can himself monitor and predict the effect of the treatment he is to follow on the behaviour of his blood glucose level.

Another purpose of the invention is to provide a monitoring equipment which facilitates and improves the treatment of a patient. This object is achieved with a monitoring equipment according to the invention, characterized in that the monitoring equipment comprises means for receiving data concerning at least the patient's diet, medication and physical strain and for storing the data in the first memory means, data processing means for calculating a predictive value on the basis of the data stored in the first memory means, the predictive value indicating the patient's predictable blood glucose level at a predetermined moment, and corrector means for calculating the difference between the calculated predictive value and the patient's actual blood glucose level calculated at said predetermined moment, and for correcting the mathematical model utilized by the data processing means to calculate a predictive value in order to take into account said difference in the subsequent calculations of predictive values.

The invention is based on the idea that when an adaptive mathematical model is formulated concerning the behaviour of a patient's blood glucose level and when the patient is provided with a monitoring equipment comprising data processing means for calculating a predictive value describing the patient's blood glucose level on the basis of data supplied to the equipment, and corrector means for correcting the model used for calculating the predictive value on the basis of the difference between the previous predictive values and the actual measurement results, the patient can take care of himself better than before and monitor and predict the development of his own health, since he is able to better estimate, by means of the monitoring equipment, how his blood glucose level is likely to change on the basis of the predictable medication, diet and physical strain. In other words, if the predictive value turns out to be bad, the patient can contact for example his doctor in order to discuss possible changes in medication or he can alternatively change his diet, for instance.

Due to the corrector means the monitoring equipment becomes adaptive, i.e. it can take into account the characteristic features of the patient in question in the mathematical model utilized by the data processing means, so that the differences between the previous predictive values and the actual measurement results can be used in the long term to develop a mathematical model for the patient in question. If the mathematical model used for calculating a predictive value turns out to be very accurate in the long term due to the action of the corrector means, i.e. if the difference between the predictive value and the actual value measured afterwards is close to zero, the patient can even skip some measurements due to the monitoring equipment according to the invention, since he can accurately predict with the equipment the development of the glucose level by means of the expected diet, medication and physical strain. This considerably facilitates the situation for the patient since the blood glucose level is rather complicated to measure.

The method and the monitoring equipment according to the invention therefore have the following primary advantages. The method and the monitoring equipment considerably improve and facilitate the patient's self-care since the patient can estimate the development of his blood glucose level better than before. The doctor obtains more detailed and more accurate data about the patient's health since it is possible to read from the memory of the monitoring equipment data that the doctor can utilize later for example for a trend analysis. Due to the monitoring equipment, the number of the daily glucose level measurements can be decreased in the long term.

In a preferred embodiment of the monitoring equipment according to the invention, the monitoring equipment consists of a data processing equipment of a hospital or the like with which the patient communicates via a communications device utilizing wireless data transmission. This embodiment of the invention makes it possible for the patient to transmit the required data to the monitoring equipment regardless of his current location. This embodiment also enables for the doctor to monitor, if desired, the most recent data concerning the patient's health without a need for an appointment, or even a phone call, between the patient and the doctor.

In another preferred embodiment of the monitoring equipment according to the invention, the monitoring equipment and the measuring equipment suitable for measuring the blood glucose level are integrated into a communications device, preferably a mobile phone, utilizing wireless data transmission. This embodiment of the invention frees the patient from carrying with him several separate conspicuous devices, since only one device is sufficient. Also in this embodiment the patient can continuously transmit, via the communications device, data concerning his health to the doctor treating him, regardless of the patient's location, and the doctor can monitor the development in the patient's health and even contact the patient directly by means of the mobile phone, if required. In this embodiment, the calculation of the predictive value is naturally not dependent on whether the patient is located in a shadow area of the mobile system at the moment, since the calculation of the predictive value takes place entirely in the monitoring equipment the patient carries with him. If the patient is in a shadow area at the moment of calculation, he can transmit afterwards, if he so wishes, the data that he has supplied to the monitoring equipment and that has been stored in the memory thereof to the data processing system available to the doctor treating him.

The preferred embodiments of the monitoring equipment according to the invention are disclosed in the appended dependent claims 3 to 7.

BRIEF DESCRIPTION OF THE DRAWINGS

In the following, the invention will be described in greater detail, by way of an example, by means of a few preferred embodiments of the invention illustrated in the accompanying figures, in which FIG. 1 illustrates the first preferred embodiment of the monitoring equipment according to the invention, FIGS. 2 and 3 illustrate the second preferred embodiment of the monitoring equipment according to the invention, and FIG. 4 illustrates the calculation of a predictive value.

DESCRIPTION OF THE PREFERRED EMBODIMENTS

FIG. 1 illustrates the first preferred embodiment of the monitoring equipment according to the invention. In the case shown in FIG. 1, the monitoring equipment consists of a hospital data processing system 9 and the applications software used therein.

In the situation shown in FIG. 1, the patient can use a mobile phone 1 by means of which he can supply data to the monitoring equipment 9. When the patient wants the monitoring equipment 9 to calculate a predictive value for the likely blood glucose level at a certain moment, for example after five hours, he supplies data concerning at least the most recent measurement result and the time of the measurement (if the data concerning the measurement result has not been supplied before to the monitoring equipment), the expected medication, diet, physical strain and the moment for which the predictive value is to be calculated (i.e. in this example five hours later) to the monitoring equipment 9 via the keyboard of the mobile phone 1. If the mobile phone comprises an integrated measuring device for measuring the glucose level, the measurement result or the time of the measurement do not have to be supplied since they may be stored in the memory of the mobile phone 1. The mobile phone 1 that is assumed to be, by way of an example, a mobile phone of the GSM mobile system (Groupe Spécial Mobile) then transmits the supplied data in the form of a short message 3 to a base station 4. The base station 4 forwards the message via a base station controller 5, a mobile services switching centre (MSC) 6 and a gateway centre 7 to a short message service centre (SMSC) 8 in the mobile system. The GSM system and the short message service thereof are described in greater detail for example in *The GSM System for Mobile Communications* by M. Mouly and M.-B. Pautet, Palaiseau, France, 1992, ISBN: 2-9507190-0-7, and therefore they will not be described in greater detail in this connection.

The short message service centre 8 is programmed to transmit the short message received from the patient's mobile phone 1 directly to the data processing system 9 of the hospital. Therefore the doctor treating the patient has at all times access to the most recent data concerning the patient, regardless of the patient's current location.

When the monitoring equipment 9 has received, via its transceiver unit 15, the data supplied by the patient, it stores it in a first memory means 10 that may consist of, for example, a file in the hard disk of a computer. A calculator 12 thereafter starts calculating a predictive value on the basis of the data stored in the first memory means. During the calculation, the calculator 12 also takes into account correction coefficients stored in a second memory means 11. The first 10 and the second 11 memory means may consist of, for example, separate storage locations situated physically in the same memory chip, or alternatively of separate files located in the same computer hard disk. The calculation of a predictive value is described in greater detail in connection with FIG. 3.

When the predictive value has been calculated, the monitoring equipment 9 transmits it in the form of a short message to the patient's mobile phone 1, and the patient can ensure by means of the predictive value that his blood glucose level remains within the allowable area for the next five hours. On the other hand, if the predictive value shows that the blood glucose level is likely to change unfavourably during the following, for example five, hours, the patient may consider changing his diet, physical strain or even medication and he can supply the new changed data to the monitoring equipment and obtain a new predictive value which indicates the effect of the change on the blood glucose level.

Next time when the patient measures the blood glucose level and supplies the data concerning the measurement value and the moment of measurement to the monitoring equipment 9, the equipment stores this data into the first memory means 10 and also uses this data for correcting the mathematical model used for calculating the predictive value.

If the most recent moment of measurement corresponds to the moment for which the calculator 12 has already previously calculated a predictive value, the calculator 12 retrieves from the memory 10 this value and supplies it to the corrector 13. The corrector 13 thereafter calculates the difference between the predictive value and the measurement value. On the basis of this difference, the corrector 13 changes the correction coefficients used for calculating the predictive value in such a way that if the calculator would calculate a new predictive value with the same initial values stored in the memory means 10 but with the new correction coefficients, the difference between the predictive value and the measured value would be smaller than before. The new correction coefficients are stored in the second memory means 11 from which the calculator 12 retrieves them for the next calculation of a predictive value.

If the most recent moment of measurement does not correspond to the moment for which the calculator 12 has already before calculated a predictive value, the calculator 12 first calculates a new predictive value for this moment of measurement on the basis of the data stored in the memory means 10. The corrector 13 thereafter calculates the difference between the predictive value and the measurement value and new correction coefficients in the above-described manner.

If the difference between the measurement value and the predictive value calculated for example for a certain time of day is repeatedly very close to zero in the long term (for several weeks), the monitoring equipment 9 may find that the predictive value is sufficiently accurate for the time of day. In such a case, the monitoring equipment 9 may suggest to the patient for example with a short message that there is no need to measure the blood glucose level at the aforementioned moment. Therefore, the patient can decrease the number of the daily measurements one at a time as the mathematical model proves to be sufficiently accurate, until as few as 1 or 2 measurements are required each day. This considerably facilitates the patient's daily life compared to the 6 to 8 daily measurements required at present for achieving a balance.

FIGS. 2 and 3 illustrate the second preferred embodiment of the monitoring equipment according to the invention. In the case shown in FIGS. 2 and 3, the monitoring equipment 9' is connected to a mobile phone.

The mobile phone MS may be for example a conventional GSM mobile phone the battery space of which comprises, instead of a conventional battery, a unit 14' which contains integrated both a battery and components required for calculating a predictive value, these components including for example a calculator 12', a corrector 13' and memory means 10' and 11'. Since the unit 14' is connected to a communication bus of the mobile phone MS, it is possible to supply data required for calculating a predictive value to the calculator 12' by means of the keyboard 15' of the mobile phone. Correspondingly, the calculator 12' may forward the calculated predictive value to the user via the display 16' of the mobile phone. Therefore, the calculation of a predictive value does not require communication with a separate data processing equipment, but the monitoring equipment 9' can independently calculate a predictive value on the basis of the data supplied thereto. However, if the patient desires he can also transmit the data he supplied to the monitoring equipment, including the latest measurement results, to the data processing system available to the doctor treating him by means of a short message.

The unit 14' preferably also comprises an integrated measuring device (not shown in the figures) known per se for measuring the glucose level of a blood sample. Therefore, the patient does not have to carry with him several separate instruments, but the mobile phone/monitoring equipment alone is sufficient.

FIG. 4 illustrates the calculation of a predictive value. According to the invention, the calculation of a predictive value can utilize any adaptive mathematical model known per se, wherein the difference between the calculated predictive value and the actual measurement result can be used for correcting the mathematical model in such a way that the difference between the calculated predictive values and the actual measurement results will be minimized in the long term. In other words, the mathematical model is able to "learn" how the patient's system, i.e. the blood glucose level, varies when certain initial values are changed. An example of a mathematical model known per se that can be utilized in the monitoring equipment according to the invention is a so-called Widrow's adaptive LMS (Least Means Square) algorithm.

In FIG. 4, basic data X which may include data about the moment $t_i$ for which the predictive value is to be calculated, the latest measurement result, the moment of measurement, and the estimated medication, diet and physical strain of the patient is supplied to the mathematical model H. The mathematical model of FIG. 4 utilizes the fact that the blood glucose level of a person with diabetes usually follows a certain daily pattern with a certain accuracy, i.e. the glucose level follows the daily routine of the diabetic approximately in the same manner from one day to another. Therefore, the effect of different initial values on the glucose level can be monitored in the long term by keeping a record of the initial values and the actual measurement values. The mathematical model can therefore be amended in such a way that the model provides a more accurate predictive value. In practice, this may take place for example in such a manner that for each moment in the daily routine there is a separate correction table wherein each initial value has its own correction coefficient, i.e. for example a weighting coefficient, which is utilized when calculating a predictive value and the value of which is changed when the real difference between the calculated predictive value and the actual measurement value is known.

In the situation shown in FIG. 4, a predictive value for the moment ti can be calculated for example from the formula $\hat{g}(t_i)=H*X$. The calculated predictive value is thereafter stored in the memory until the actual measurement value for the patient at the moment $t_i$ is obtained. When the actual measurement value $g(t_i)$ is known, the difference between the predictive value and the measurement value is calculated, i.e. $e(t_i)=g(t_i)-\hat{g}(t_i)$. The difference is utilized for correcting the mathematical model H, for example in such a way that the correction coefficients used in the model are corrected by means of the formula $h_{ik+1}=h_{ik}+2*\mu*e(t_i)*x_i(t_i)$, wherein $h_{ik}$ is the weighting coefficient of the initial value $x_i$ used in the calculation at the moment $t_i$, and $\mu$ is a small positive constant which ensures that the model does not change radically on the basis of one single calculation, but its coefficients change with relatively small steps towards optimal values.

It should be understood that the above description and the related figures are only intended to illustrate the present invention. Different variations and modifications of the invention will be evident for those skilled in the art without departing from the scope and spirit of the invention disclosed in the appended claims.

We claim:

1. A method for predicting the glucose level in a patient's bloods, the method comprising the steps of:

formulating an adaptive mathematical model about the behavior of the patient's blood glucose level, the model taking into account at least the patient's diet, medication and physical strain and providing predictive values;

providing the patient with means for utilizing said mathematical model, so that the patient can himself monitor and predict the effect of the treatment he is to follow on the behavior of his blood glucose level; and comparing the predictive values provided by the model to measured glucose levels and correcting the mathematical model on the basis of the result of said comparison.

2. A monitoring equipment for predicting the glucose level in a patient's blood, the equipment comprising:

means for receiving a measurement result indicating the glucose level in a sample of the patient's blood and for storing the measurement result in a first memory means together with data indicating the moment of the measurement, means for receiving data concerning at least the patient's diet, medication and physical strain and for storing the received data in the first memory means, data processing means for calculating a predictive value using a mathematical model taking into account the data stored in the first memory means, the predictive value indicating the patient's predicted blood glucose level at a predetermined moment, and corrector means for calculating the difference between the calculated predictive value and the patient's actual blood glucose level measured at said predetermined moment, and for correcting the mathematical model utilized by the data processing means to calculate a predictive value in order to take into account said difference in subsequent calculations of predictive values.

3. Monitoring equipment according to claim 2, wherein the data processing means comprises:

second memory means for storing correction coefficients utilized in the calculation of the predictive value, and means for searching from the second memory means, the correction coefficients corresponding to the data stored in the first memory means, and to utilize said correction coefficients in the calculation of the predictive value, the corrector means being arranged to change the value of the correction coefficients used in the calculation in order to minimize the difference between the predictive value and the glucose level measured at said predetermined moment, and to store said changed correction coefficients in the second memory means.

4. Monitoring equipment according to claim 2, wherein said means for receiving data, said data processing means, and said corrector means are included in a data processing system of a hospital or a health care center, wherein the equipment further comprises a communications device that is available to the patient and that utilizes a wireless data transmission link, wherein the means for receiving data concerning the measurement result, moment of measurement, diet, medication and physical strain comprises means for receiving said data from said communications device, and wherein the monitoring equipment comprises transmitter means for transmitting the calculated predictive value to the communications device available to the patient.

5. Monitoring equipment according to claim 2, further comprising a measuring unit for measuring the glucose level of a patient's blood sample, and for storing the data indicating the measurement result and the moment of measurement in the first memory means.

6. Monitoring equipment according to claim 5 and comprising a communications device connected to the measuring unit, the communications device comprising a mobile phone of a cellular radio system or to a two-way pager, the monitoring equipment further comprising means for transmitting the data stored in the first memory means via said communications device to a data processing system that is available to a person treating the patient, wherein the measuring unit and a battery of the mobile phone or two-way pager are integrated into one component that fits into a battery space of the mobile phone or two-way pager.

7. Monitoring equipment according to claim 2, further comprising a measuring unit for measuring the glucose level of a patient's blood sample, and for storing the data indicating the measurement result and the moment of measurement in the first memory means, and a communications device connected to the measuring unit, the communications device including a mobile phone of a cellular radio system or a two-way pager, and means for transmitting the data stored in the first memory means via said communications device to a data processing system that is available to a person treating the patient.

* * * * *

UNITED STATES PATENT AND TRADEMARK OFFICE
CERTIFICATE OF CORRECTION

PATENT NO. : 5,840,020
DATED : November 24, 1998
INVENTOR(S) : HEINONEN ET AL.

It is certified that error appears in the above-indentified patent and that said Letters Patent is hereby corrected as shown below:

On the Title Page, Item [57], in the Abstract,
    line 1, "means" should read --a transceiver unit--;
    line 3, "staring" should read --storing--; and after "memory" delete "means";
    line 5, "monitoring equipment" should read --transceiver unit--; and "includes means for receiving" should read --receives--;
    line 7, "for storing" should read --stores--; and after "memory" delete "means, data" and insert --.--.
    line 8, "processing means" should read --The monitoring equipment further includes a data processor--;
    line 9, after "memory", delete "means";
    line 10, "corrector means" should read --a corrector--; and
    line 12, after "level" delete ",".

In Claim 1, column 6, line 62, "bloods" should read --blood--;
    column 7, before line 1, the subparagraph, --programming monitoring equipment with said mathematical model-- should be inserted;
    line 1, "utilizing" should read --entering at least diet, medication, and physical strain data into--;
    line 2, "model, so that" should read --model on said monitoring equipment, and means for measuring glucose levels and for inputting said glucose levels into said mathematical model on said monitoring equipment, so that--;
    line 4, after "level;", "and" should be deleted;
    between lines 4 and 5. the subparagraph --computing predictive values with said monitoring equipment based on the data input by said patient; and-- should be inserted; and
    line 6, "measured" should read --said measured--.

UNITED STATES PATENT AND TRADEMARK OFFICE
CERTIFICATE OF CORRECTION

PATENT NO. : 5,840,020
DATED : November 24, 1998
INVENTOR(S) : HEINONEN ET AL.

It is certified that error appears in the above-identified patent and that said Letters Patent is hereby corrected as shown below:

In Claim 2, column 7, line 8, "A monitoring" should read --Monitoring--.

Signed and Sealed this

Twenty-third Day of March, 1999

Attest:

Attesting Officer

Q. TODD DICKINSON

Acting Commissioner of Patents and Trademarks